United States Patent [19]

Irie et al.

[11] Patent Number: 5,298,141

[45] Date of Patent: Mar. 29, 1994

[54] APPARATUS FOR MEASURING CONCENTRATION OF NON-VOLATILE INGREDIENTS

[75] Inventors: Tomoyuki Irie, Osaka; Ikuo Tochizawa, Kawanishi, both of Japan

[73] Assignee: Nippon Paint Co., Ltd., Osaka, Japan

[21] Appl. No.: 960,398

[22] PCT Filed: May 21, 1992

[86] PCT No.: PCT/JP92/00654

§ 371 Date: Jan. 15, 1993

§ 102(e) Date: Jan. 15, 1993

[87] PCT Pub. No.: WO92/21022

PCT Pub. Date: Nov. 26, 1992

[30] Foreign Application Priority Data

May 23, 1991 [JP] Japan ................... 3-149700

[51] Int. Cl.$^5$ ............................. C25D 13/24
[52] U.S. Cl. .................. 204/299 EC; 204/180.8; 73/61.79; 73/64.53
[58] Field of Search .......... 204/180.1, 180.8, 299 EC; 73/61.49, 61.79, 64.53

[56] References Cited

U.S. PATENT DOCUMENTS

| | | | |
|---|---|---|---|
| 3,954,119 | 5/1976 | Kunioka et al. | 72/236 |
| 4,097,358 | 6/1978 | Wiseman | 204/270 |
| 4,160,716 | 7/1979 | Wiseman | 204/270 |

FOREIGN PATENT DOCUMENTS

| | | |
|---|---|---|
| 55-152445 | 11/1980 | Japan . |
| 291717 | 12/1986 | Japan . |
| 96296 | 4/1988 | Japan . |
| 2-150767 | 6/1990 | Japan . |
| 05565 | 1/1992 | Japan . |

Primary Examiner—John Niebling
Assistant Examiner—Kishor Mayekar
Attorney, Agent, or Firm—Beveridge, DeGrandi, Weilacher & Young

[57] ABSTRACT

An apparatus for measuring concentration of non-volatile ingredients in a liquid-type material comprises a debubbling device for removing air bubbles contained in the liquid-type material, and a calculator which obtains a non-volatile ingredient concentration measurement of the liquid-type material from which air bubbles have been removed by the debubbling device.

19 Claims, 6 Drawing Sheets

APPARATUS FOR MEASURING CONCENTRATION OF NON-VOLATILE INGREDIENTS

TECHNICAL FIELD

The present invention relates to a concentration measuring apparatus, and more particularly, to an apparatus for measuring concentration of non-volatile ingredients in a liquid-type material.

BACKGROUND ART

A liquid-type material such as a resin suspension or cement sludge comprises volatile ingredients and non-volatile ingredients. An electrodeposition paint, for example, contains pigments and water-soluble resins as non-volatile ingredients in a volatile solvent solution which includes water and an organic solvent.

To maintain quality in working with such kinds of liquid-type material, it is important to control the concentration of its non-volatile ingredients. For example, when applying an electrodeposition paint onto such substrates as automobile body parts or building materials, the substrates are continuously immersed in an electrodeposition paint bath. During the application procedure, concentration of non-volatile ingredients in the electrodeposition paint falls gradually. Therefore, the concentration is periodically measured, and a specific quantity of the electrodeposition paint is accordingly supplied into the electrodeposition paint bath.

The concentration of non-volatile ingredients in the electrodeposition paint is usually measured according to Japanese industrial standard (JIS) K5407. This is a method comprising the steps of measuring precisely unit volume weight of the paint before and after heating, and of determining the proportion of the weight of the heated paint to that of the paint before heating. However, it takes such a long time, i.e., approximately three hours, to obtain a result by this method that it is impracticable to ascertain the real-time concentration. Consequently, when the result is obtained, the concentration of non-volatile ingredients in the electrodeposition paint bath usually has become different from that at the time of measuring, impairing accurate control of the concentration of non-volatile ingredients.

Accordingly, a variety of methods and apparatus for rapidly measuring concentration of non-volatile ingredients have been furnished. Japanese Laid-Open Patent Application No. 263297/1989, and Bänder Bieche Rohre 3-1990, p. 41&ff., disclose a method for calculating concentration of non-volatile ingredients from the velocity of ultrasound passed through an electrodeposition paint. Japanese Laid-Open Patent Application Nos. 150767/1990 and 5565/1992 further disclose a method for calculating concentration of non-volatile ingredients from a damping factor of ultrasound passed through an electrodeposition paint.

However, accurate calculation of the concentration of non-volatile ingredients is impeded in the foregoing methods as well. This is because the ultrasound is scattered by air bubbles in the electrodeposition paint, generating noise. In other words, air bubbles in an electrodeposition paint interfere with the accurate measurement of both the ultrasound velocity and the damping factor.

In an electrodeposition paint, the ultrasound damping factor is linearly proportional to the concentration of non-volatile ingredients if pH, temperature and solvent concentration of the electrodeposition paint are stable, such that it is possible to ascertain accurately the concentration of non-volatile ingredients in the paint immediately from the damping factor, if the relationship between damping factor and concentration of non-volatile ingredients is previously determined. However, in an actual measuring procedure, the pH and other factors may not be stabilized, such that the damping factor will not always be linearly proportional to the concentration of non-volatile ingredients; it thus becomes unfeasible to determine accurately the concentration of non-volatile ingredients only from the damping factor.

SUMMARY OF THE INVENTION

It is an object of the present invention to obtain a reliable measurement of the concentration of non-volatile ingredients in a liquid-type material from the velocity of ultrasound passed therethrough, or from an ultrasonic damping factor therein.

It is an another object to provide a method for obtaining a reliable measurement of the concentration of non-volatile ingredients in an electrodeposition paint, from the velocity of ultrasound passed therethrough, or from an ultrasonic damping factor therein.

It is yet another object of the present invention to provide a method for accurately controlling the concentration of non-volatile ingredients in a liquid-type material.

It is a further object to provide a cyclone of simple construction capable of efficiently removing air-bubbles from a liquid-type material.

An apparatus according to one aspect of the present invention is for calculating the concentration of non-volatile ingredients in a liquid-type material. The apparatus comprises debubbling equipment for removing air-bubbles from the liquid-type material, and measuring equipment for obtaining a measurement of the concentration of non-volatile ingredients in the liquid-type material, having had air-bubbles therein removed by the debubbling equipment.

In the first place, the debubbling equipment of the apparatus removes air bubbles from a given liquid-type material, and then measurement of the concentration of non-volatile ingredients therein is obtained by the measuring equipment. Therefore, air bubbles do not remain in the liquid-type material to interfere with the measuring equipment, and the apparatus gives a reliable measuring result.

A method according to another aspect of the present invention is for measuring the concentration of non-volatile ingredients in an electrodeposition paint. The method comprises the steps of: measuring an ultrasonic damping factor of ultrasound passed through the electrodeposition paint; and calculating concentration of non-volatile ingredients from the damping factor according to the following expression (1):

$$NV(\%) = \{dB + \beta(\Delta t) + \gamma(\Delta pH) + \delta(\Delta c)\}/\alpha \tag{1}$$

wherein
NV (%) is percent concentration of non-volatile ingredients;
dB is the damping factor value measured in decibels;
$\alpha$ is a coefficient $dB_\alpha/NV_\alpha$ of the damping factor;
$\beta$ is a temperature-correction coefficient, $dB_\beta/\Delta t_\beta$;
$\gamma$ is a pH-correction coefficient, $dB_\gamma/\Delta pH_\gamma$;

δ a solvent-concentration correction coefficient, $dB_\delta/\Delta C_\delta$;

$\Delta t$, $\Delta pH$, and $\Delta C$ are the difference between reference temperature, pH, and solvent concentration, respectively, for the liquid-type material, and measured real-time values thereof.

In this method, the relational expression between the ultrasonic damping factor and the concentration of non-volatile ingredients in an electrodeposition paint is defined by considering changes in pH, temperature and solvent concentration. In applying the relational expression, if a damping factor coefficient, a temperature-correction coefficient a pH-correction coefficient and a solvent-correction coefficient are previously determined with respect to given kinds of electrodeposition paint, accurate calculation of the concentration of non-volatile ingredients in an electrodeposition paint is made from the real-time damping factor, despite changes in other factors such as pH during the measuring procedure.

A method according to a further aspect of the present invention is for measuring the concentration of non-volatile ingredients in a electrodeposition paint. The method comprises the steps of: measuring an ultrasonic damping factor of ultrasound passed through the electrodeposition paint; and calculating concentration of non-volatile ingredients from the damping factor according to the following expression (2):

$$NV(\%) = \{dB + X(\Delta t)\}/\alpha \quad (2)$$

wherein

NV (%) is percent concentration of non-volatile ingredients;

dB is the damping factor value measured in decibels;

X is a coefficient within the range of 0.36 to 0.46;

$\Delta t$ is the difference between a reference temperature for the liquid-type material, and a real-time temperature thereof; and $\alpha$ is a coefficient $dB_\alpha/NV_\alpha$ of the damping factor.

In this method, the relational expression between the ultrasonic damping factor and the concentration of non-volatile ingredients in an electrodeposition paint is defined by considering changes in pH, temperature and solvent concentration. In applying the relational expression, if only a damping factor coefficient, is previously determined with respect to given kinds of electrodeposition paint, accurate calculation of the concentration of non-volatile ingredients in an electrodeposition paint is made from the real-time damping factor, despite changes in other factors such as pH during the measuring procedure.

A still further aspect of the present invention defines a method for controlling, in an electrodeposition paint contained in a bath vessel, concentration of its non-volatile ingredients contained therein together with its volatile ingredients. The method comprises the steps of: measuring an ultrasonic damping factor of ultrasound passed through the electrodeposition paint; calculating concentration of non-volatile ingredients from the damping factor according to the following expression (1); and supplying specific quantities of the volatile and non-volatile ingredients into the bath vessel according to the result obtained from the calculation.

$$NV(\%) = \{dB + \beta(\Delta t) + \gamma(\Delta pH) + \delta(\Delta c)\}/\alpha \quad (1)$$

wherein

NV (%) is present concentration of non-volatile ingredients;

dB is the damping factor value measured in decibels;

$\alpha$ is a coefficient $dB_\alpha/NV_\alpha$ of the damping factor;

$\beta$ is a temperature-correction coefficient, $dB_\beta/\Delta + \beta$;

$\gamma$ is a pH-correction coefficient, $dB_\gamma/\Delta ph_\gamma$;

δ a solvent-concentration correction coefficient, $dB_\delta/\Delta C_\delta$;

$\Delta t$, $\Delta pH$, and $\Delta C$ are the difference between reference temperature, pH, and solvent concentration, respectively, for the liquid-type material, and measured real-time values thereof.

Through this method, a real-time calculation providing a measurement of the concentration of non-volatile ingredients in an electrodeposition paint contained in a bath vessel is made according to the expression (1) from the damping factor, so that it is practicable to ascertain variation in the concentration without delay. Thus, when the concentration of non-volatile ingredients changes, correct proportions of the paint ingredients are restored immediately by supplying regulated quantities of volatile and non-volatile ingredients into the vessel according to the extent by which the concentration has varied.

A method according to yet a further aspect of the present invention defines a method for controlling, in an electrodeposition paint contained in a bath vessel, concentration of its non-volatile ingredients contained therein together with its volatile ingredients. The method comprises the steps of: measuring an ultrasonic damping factor of ultrasound passed through the electrodeposition paint; calculating concentration of non-volatile ingredients from the damping factor according to the following expression (2); and supplying specific quantities of the volatile and non-volatile ingredients into the bath vessel according to the result obtained from the calculation.

$$NV(\%) = \{dB + X(\Delta t)\}/\alpha \quad (2)$$

wherein

NV (%) is percent concentration of non-volatile ingredients;

dB is the damping factor value measured in decibels;

X is a coefficient within the range of 0.36 to 0.46;

$\Delta t$ is the difference between a reference temperature for the liquid-type material, and a real-time temperature thereof; and $\alpha$ is a coefficient $dB_\alpha/NV_\alpha$ of the damping factor.

Through this method, a real-time calculation providing a measurement of the concentration of non-volatile ingredients in an electrodeposition paint contained in a bath vessel is made according to expression (2) from the damping factor, so that it is practicable to ascertain variation in the concentration without delay. Thus when the concentration on non-volatile ingredients changes, correct proportions of the paint ingredients are restored immediately by accordingly regulated supply of volatile and non-volatile ingredients into the bath vessel.

According to a still further aspect of the present invention, a cyclone provided for removing air bubbles contained in a liquid-type material comprises an upright cylindrical main body at the opposing ends of which are respective upper and lower circular conic sections each having an apical outlet, and further includes an inlet mounted on the upper conic section, through which the liquid-type material is tangentially introduced into the main body.

In the cyclone, the greater portion of a liquid-type material introduced into the main body through the inlet forms a spiral vortex descending along the inner circumferential surface of the main body, which then is expelled through the apical outlet in the lower conic section. Meanwhile, a lesser portion of the liquid-type material forms a spiral vortex ascending in the main body, which consequently is ejected through the apical outlet in the upper conic section. Concurrently, air bubbles contained in the liquid-type material gather toward the center of the main body, due to their lighter weight. Thus, the bubbles rise in the main body, following the ascending spiral vortex, and then are ejected from the upper apical outlet together with the liquid-type material. Therein, the bubbles readily separate from the liquid-type material and gather toward the apex of the upper conic section of the main body, since the dynamic pressure of the ascending spiral vortex becomes nearly constant both centrally and superficially, within the correspondingly circular conic configuration of the upper section. The cyclone thus continuously and effectively removes air bubbles from liquid-type material.

According to yet a further aspect, a cyclone provided for removing air bubbles contained in a liquid-type material comprises a main body, formed as a hollow circular cone having respective apical and base outlets and mounting an inlet through which liquid-type material is tangentially introduced.

In the cyclone, the greater portion of a liquid-type material introduced into the main body forms a spiral vortex which descends along the main body inner circumferential surface and then is ejected from the base outlet. A lesser portion of the liquid-type material forms an ascending spiral vortex, meanwhile gathering along the lightweight air bubbles centrally of the main body, such that they are expelled together with the liquid-type material from the apical outlet. Therein, the bubbles readily separate from the liquid-type material and gather toward the apex of the upper conic section of the main body, since the dynamic pressure of the ascending spiral vortex becomes nearly constant both centrally and superficially, within the correspondingly circular conic configuration of the upper section. The cyclone thus continuously and effectively removes air bubbles from liquid-type material.

The foregoing and other objects and advantages of the present invention will be more fully apparent from the following detailed description.

DESCRIPTION OF THE PREFERRED EMBODIMENTS

Figure 1:
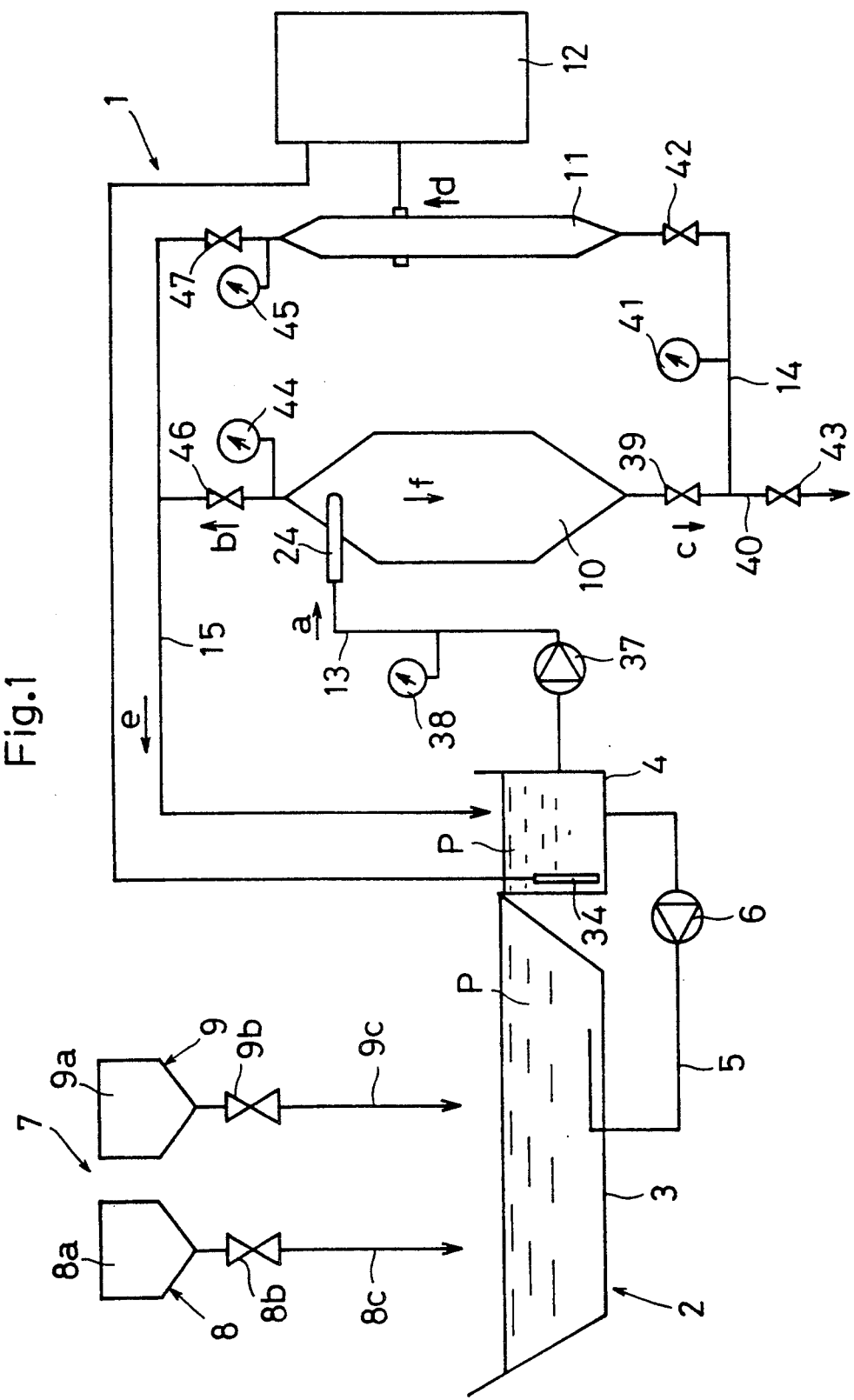
FIG. 1 is a schematic view of the structure of an apparatus according to an embodiment of the invention.

FIG. 1 illustrates a non-volatile ingredient concentration measuring apparatus 1 in accordance with one embodiment of the invention. An electrodeposition paint bath 2 is equipped with the concentration measuring apparatus 1. In the figure, the apparatus 1 is shown exaggerated relative to the paint bath 2 to aid comprehension.

The paint bath 2 comprises a bath main vessel 3 and a bath sub-vessel 4, both of which store electrodeposition paint P. The vessels 3, 4 are interconnected, wherein paint P overflowing from the bath main vessel 3 enters the bath sub-vessel 4. Additionally, a recirculation passage 5 having a circulating pump 6 is arranged between the bath main vessel 3 and the bath sub-vessel 4. The recirculation passage 5 returns overflow paint P from the bath main vessel 3 to the bath sub-vessel 4, thus recirculating the paint P between the bath main vessel 3 and the bath sub-vessel 4. Furthermore, supply equipment 7, comprising a pigment supplier 8 and a resin supplier 9 having tanks 8a and 9a, respectively, is arranged above the bath main vessel 3. The tank 8a stores a pigment in a solvent containing water, and the tank 9a stores a resin in a solvent containing water. The tanks 8a and 9a have respective feed lines 8c and 9c extending toward the bath main vessel 3, which in turn are provided with valves 8b and 9b respectively.

The electrodeposition paint P which is stored into the bath main vessel 3 and the bath sub-vessel 4 is an emulsion-type paint containing a pigment, a resin, a solvent and water. The pigment and the resin respectively may be, for example, carbon black or titanium oxide; and an epoxy-type cationic resin. Examples of the solvent include butyl Cellosolve, 2-ethylhexyl Cellosolve and propyleneglycol monophenyl ether.

The concentration measuring apparatus 1 mainly comprises a cyclone 10; an ultrasonic damping factor measuring device 11; operational equipment 12; a feed line 13, which feeds the electrodeposition paint P from the paint bath 2 to the cyclone 10; a manifold 14, which connects the cyclone 10 with the damping factor measuring device 11; and a feedback line 15 extending to the paint bath 2 and interconnecting both the cyclone 10 and the damping factor measuring device 11. These facilities are enclosed together in one unit.

Figure 2:
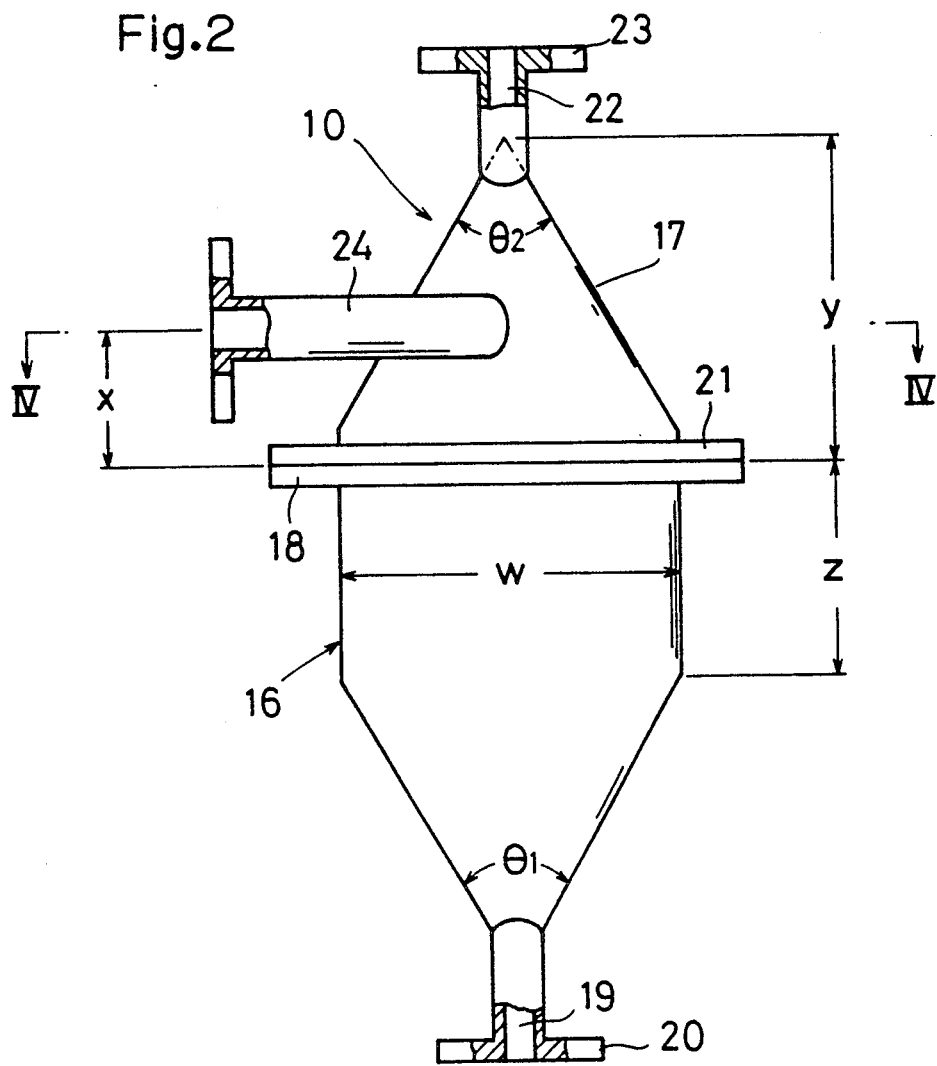
FIG. 2 is an elevational view of a cyclone employed therein.
Figure 3:
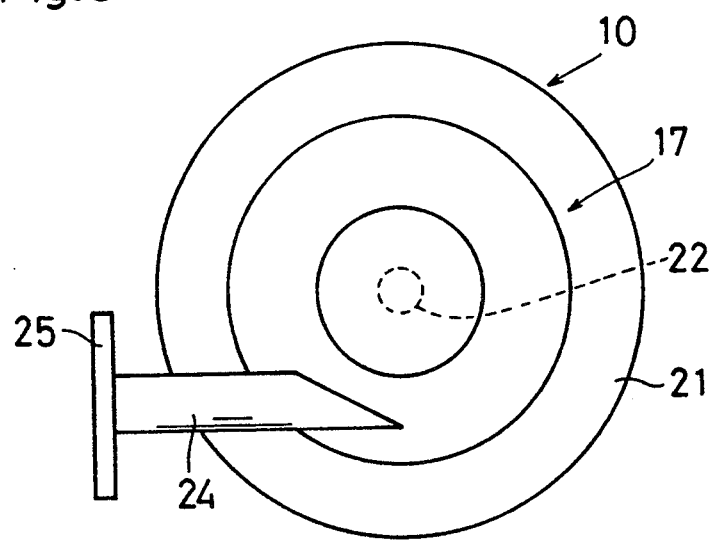
FIG. 3 is a plan view of the cyclone.
Figure 4:
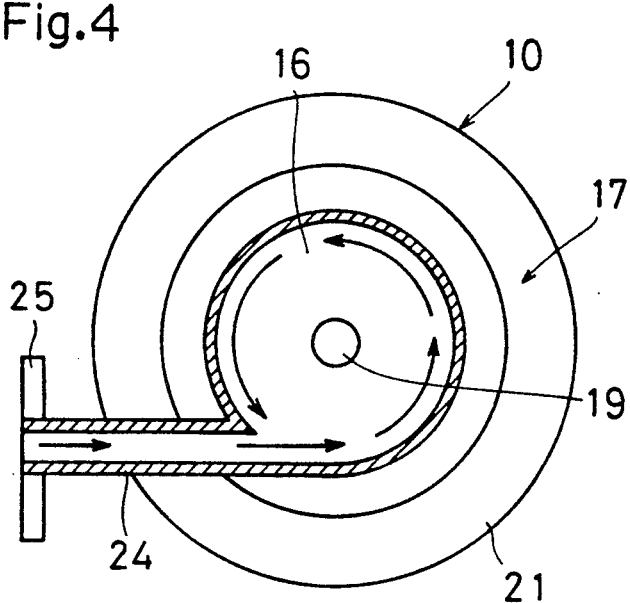
FIG. 4 is a sectional view taken along the line IV—IV of FIG. 2.

Referring to FIGS. 2 through 4, the cyclone 10 principally comprises a lower portion 16 and an upper section 17. The lower portion 16 is a cylinder adjoined to a circular conic lower section. The vertical angle $\theta_1$ of the lower section is made to be in the range of 30° to 90°; more preferably, it is set at 60°. The rim at the mouth of the lower portion 16 cylinder is a horizontally extending flange 18. At the conical vertex of the lower portion 16 is a downward-extending effluent port 19, the tip of which is flanged; and this flange 20 is connected to one end of the manifold 14, as indicated in FIG. 1.

The upper section 17 is a circular cone opening downward. The rim of the basal opening of the upper section 17 extends horizontally in a flange 21, and therein correspondingly matches the flanged mouth of the lower portion 16. The apical angle $\theta_2$ of the upper section 17 is made to be in the range of 30° to 90°; more preferably, it is set at 60°. Furthermore, an effluent port 22 extends upward form the conical apex of the upper section 17. The effluent port 22 is communicated with the feedback line 15, as indicated in FIG. 1, in its connection therewith through a flange 23 at the effluent port 22 tip. The upper section 17 is fixed onto the lower portion 16, wherein the respective axes thereof coincide.

Additionally, an introduction port 24, which introduces the electrodeposition paint P into the cyclone 10 from the feed line 13, is mounted on the upper section 17. The introduction port 24 projects horizontally, and extends tangentially along the inner circumferential surface of the upper section 17, as shown in FIGS. 3 and 4. The introduction port 24 is communicated with the feed line 13 in its connection therewith through a flange 25 at the external tip of the introduction port 24.

Dimensions x, y, w and z of the cyclone 10, as indicated in FIG. 2, are proportioned according to the following ratio:

$$x:y:w:z = 1:2.5:2.5:1.5$$

The ultrasonic-damping factor measuring device 11 is cylindrical in form, and is vertically disposed. The remaining ends of the manifold 14 and of the feedback line 15 are connected with respective lower and upper ends of the device 11, whereby flow of the electrodeposition paint P is from the manifold 14 through the device 11 to the feedback line 15.

Figure 5:
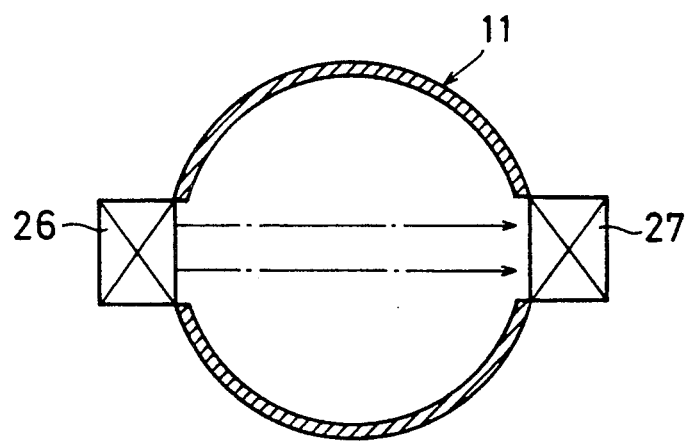
FIG. 5 is a cross-sectional view of an ultrasonic-damping factor measuring device employed in the embodiment.

Referring to FIG. 5, the measuring device 11 is furnished with an ultrasonic generator 26, and an ultrasonic detector 27 diametrically opposite thereto. The generator 26 emits ultrasonic waves of 3 MHz or 2 MHz, for example, toward the ultrasonic detector 27, which is receptive of the waves, but which in particular will thoroughly detect the ultrasonic waves only when volatile ingredients of the electrodeposition paint P, i.e. a solvent and water, are flowing inside the measuring device 11.

Figure 6:
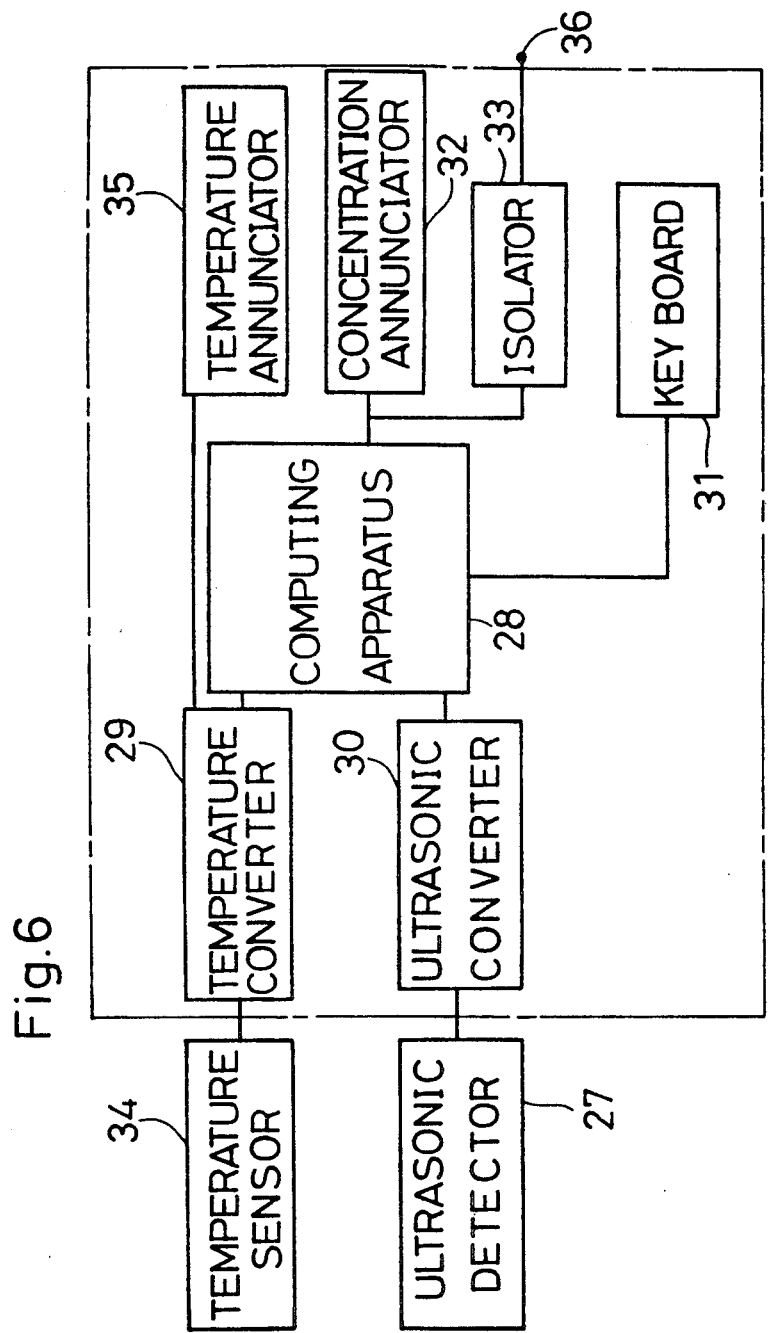
FIG. 6 is a block diagram representing operational equipment employed therein.

The operational equipment 12 includes a computing apparatus 28 as indicated in FIG. 6. The computing apparatus 28 principally comprises a central processing unit (CPU), a read only memory (ROM), a random access memory (RAM) and an I/O device. The ROM stores a program for calculating a non-volatile ingredient concentration measurement which includes the following operator expression (2):

$$NV(\%) = \{dB + X(\Delta t)\}/\alpha \qquad (2)$$

wherein
  NV (%) is percent concentration of non-volatile ingredients;
  dB is the damping factor value of ultrasound passed through the electrodeposition paint P, and measured in decibels by the damping factor measuring device 11;
  α is a damping factor coefficient;
  Δt is the difference between a reference temperature for the paint P, and a real-time temperature measured thereof; and
  X represents a coefficient within the range of 0.36 to 0.46.

The damping factor coefficient α is calculated by dividing an ultrasonic damping factor (dB) of the paint P by the percent concentration of its non-volatile ingredients (NV), measured according to JIS K5407. The coefficient α corresponds to coefficient A in the formula dB=A·NV, given that the proportional relationship between NV and dB is accordingly established. Each type of electrodeposition paint P will have a characteristic coefficient α; thus the ROM stores the coefficient α of the electrodeposition paint P frequently used. However, the coefficient α of any particular electrodeposition paint that is the material of the concentration measurement can be input into the computing apparatus 28 via a keyboard 31, as mentioned later. The reference temperature upon which Δt is based is the temperature of the electrodeposition paint P at the time that the damping factor coefficient α is determined, and is normally 28° C.

The foregoing operator expression will be described in more detail in the following.

Output ports of both a temperature converter 29 and an ultrasonic converter 30, as well as a keyboard 31 are connected with the input ports of the I/O device of the computing apparatus 28; and a concentration annunciator 32 and an isolator 33 are connected with its output ports. An input port of the temperature converter 29 is connected with a temperature sensor 34. The converter 29 converts an analog signal from the temperature sensor 34 into a digital signal. Another output port of the temperature converter 29 is directly connected with a temperature annunciator 35. The temperature sensor 34 may be a thermocouple or a resistance bulb, and is disposed in the bath sub-vessel 4 as indicated in FIG. 1. The temperature annunciator 35 routinely indicates temperature measured by the temperature sensor 34. An input, port of the ultrasonic converter 30 is connected with the ultrasonic detector 27 of the damping factor measuring device 11. The isolator 33 has an output terminal 36. The output terminal 36 is connected with a host computer which controls the concentration measuring apparatus 1 as a whole. The concentration annunciator 32 and the temperature annunciator 35 are fixed to the enclosure housing the apparatus 1, wherein they can be seen directly from outside the unit.

The feed line 13 is connected proximally with the bath sub-vessel 4, and includes a feed pump 37 and a pressure gage 38. The feed pump 37 feeds electrodeposition paint P stored in the bath sub-vessel 4 into the cyclone 10.

The manifold 14 sends electrodeposition paint P from the cyclone 10 to the ultrasonic damping factor measuring device 11; and it includes a first valve 39, a branch pipe 40, a pressure gage 41 and a second valve 42, in that order from the cyclone 10. The branch pipe 40 is open-ended, and contains a third valve 43.

The feedback line 15 extends from both the effluent port 22 of the cyclone 10, and the upper end of the measuring device 11, and toward the bath sub-vessel 4. The feedback line 15 includes a pressure gage 44 and a fourth valve 46 near the cyclone 10, as well as a pressure gage 45 and a fifth valve 47 near the measuring device 11.

The following is a description of an operation of the apparatus 1.

A conductive substrate such as an automobile body part or stock steel is soaked in the electrodeposition paint bath 2. Upon electrifying the substrate, both the pigment and the resin in the electrodeposition paint P are superficially deposited on the substrate, forming a coating thereon. The paint P is continuously applied to the substrate in the paint bath 2, such that the concentration of pigment and resin in the electrodeposition paint P, i.e. the concentration of the non-volatile ingredients, gradually decreases over time. Therefore, it is necessary to measure the concentration of the non-volatile ingredients in the electrodeposition paint P regularly, and to maintain constant concentration by accordingly supplying pigment and resin.

Wherein the non-volatile ingredient concentration in the paint P is determined by the measuring apparatus 1, the third valve 43 is closed, and other valves 39, 42, 46 and 47 are opened. Subsequently, operating the feed pump 37, the paint P is introduced into the cyclone 10 through the introduction port 24 from the feed line 13. The electrodeposition paint P introduced into the cyclone 10 is divided into ascending and descending vortices. The paint P ascending in the cyclone 10 flows into the feedback line 15 through the effluent port 32, and then returns to the bath sub-vessel 4. Meanwhile, the paint P descending in the cyclone 10 flows into the manifold 14 through the effluent port 19, and then flows into the ultrasonic damping factor measuring device 11. The paint P flowing into the measuring device 11 ascends therein, flows into the feedback line 15, and then returns to the bath sub-vessel 4.

Regarding flow rates a, b, c, d, e and f of the electrodeposition paint P indicated in FIG. 1, it is preferable to regulate these to be within 1.0–10 m/sec., 0.1–2.0 m/sec., 0.1–1.0 m/sec., 0.05–0.5 m/sec., 1.0–5.0 m/sec., and 0.01–0.1 m/sec., respectively by adjusting the degree to which the corresponding valves 39, 41, 46 and 47 are opened. The foregoing flow rates can be adjusted according to indicated pressures on the pressure gages 38, 41, 44 and 45.

In the cyclone 10, the greater portion of the paint P introduced through the introduction port 24 is centripetally forced into a spiral vortex descending along the inner circumferential surface of the cyclone 10, as illustrated by arrows in FIG. 4. The descending paint P is then expelled from the effluent port 19 into the manifold 14. Meanwhile, a lesser portion of the paint P forms into a spiral vortex which ascends within the cyclone 10, and is then ejected through the effluent port 22 into the feedback line 15. Concurrently, air bubbles contained in the paint P separate out of it and gather toward the center of the cyclone 10, due to their lighter weight. Accordingly, the air bubbles are ejected from the effluent port 22 into the feedback line 15 together with the ascending spiral vortex of the paint P. Herein, the air bubbles readily gather toward the upper apex of the cyclone 10, namely toward the effluent port 22, owing to the circular conic configuration of the cyclone upper section 17. Consequently, air bubbles contained in the paint P are removed effectively.

The air bubbles flowing into the feedback line 15 from the cyclone 10 return to the bath sub-vessel 4 together with the paint P.

In the meantime, electrodeposition paint P, from which air bubbles have been removed by the cyclone 10 in the foregoing manner, is provided to the ultrasonic damping factor measuring device 11. Following the flow chart of FIG. 7, operation of the device 11 is described below.

When an operator activates a start switch of the keyboard 31, the program initializes the device 11 at step S1. Therein, a damping factor coefficient reference value, to be described later, and a reference temperature of the electrodeposition paint P, are set.

Following step S1, the program stands by, awaiting operator key entry. At step S2, the program determines whether the operator has activated a mode key selecting damping factor coefficient $\alpha$ set entry. Moreover, at step S3, the program determines whether a measurement-process start key has been activated. If the operator does not operate the keyboard 31, the program maintains the stand-by condition.

If the operator elects to activate the mode key on the keyboard 31 in order to set a particular coefficient $\alpha$, different from the coefficients $\alpha$ stored in the ROM, for a given electrodeposition paint P, the program shifts from step S2 to step S4. At step S4, the RAM of the computing apparatus 28 stores the coefficient $\alpha$ entered by the operator. After step S4, the program again maintains the stand-by condition.

If the operator activates the measurement-process start key, the program shifts from step S3 to step S5, at which the temperature of the electrodeposition paint P in the bath sub-vessel 4 is measured by the temperature sensor 34. The paint P temperature thus measured is converted into a digital signal by the temperature converter 29, and then stored into the RAM of the computing apparatus 28.

After step S5, the program proceeds to step S6, and obtains an ultrasonic damping factor measurement for the paint P. Therein, the ultrasonic generator 26 emits ultrasound. A portion of the ultrasonic waves issuing from the generator 26 comes into collision with non-volatile ingredients including pigment and resin in the paint P, and thereby is damped through scattering. Accordingly, ultrasonic energy received by the detector 27 is lower than that emitted from the generator 26, wherein the detector 27 determines the ultrasonic damping factor of the ultrasound passed through the electrodeposition paint P. Therein, if the paint P contained air bubbles, it would become impracticable to measure accurately the paint P damping factor, since the ultrasonic waves are further scattered about by the air-bubbles. In this embodiment, however, air bubbles in the paint P are previously removed by the cyclone 10, such that the ultrasonic detector 27 can accurately provide detection of ultrasonic damping through the paint P. The damping factor detected by the detector 27 is converted into a digital signal by the converter 30, and then stored into the RAM of the computing apparatus 28.

Next, at step S7, the program calculates the concentration of non-volatile ingredients in the paint P from both the temperature and the damping factor measured at steps S5 and S6 respectively, according to the operator expression (2). At the next step S8, the program indicates on the concentration annunciator 32 the concentration of non-volatile ingredients measured at step S7. The foregoing measuring operation is completed within a short time after the operator activates the measurement-process start key; therefore, the operator learns the concentration of non-volatile ingredients in the electro-deposition paint P in real time.

If the concentration indicated on the annunciator 32 is lower than a non-volatile ingredient reference concentration for the paint P, it is necessary to adjust the ingredient concentration of the paint P contained in the paint bath 2 to the reference value. To adjust the concentration, the valves 8b and 9b of the supply equipment 7 are handled taking the concentration indicated on the annunciator 32 into consideration. Herein, pigment and resin are supplied into the bath main vessel 3 from the tanks 8a and 9a respectively, and the concentration of the paint P non-volatile ingredients in the paint bath 2 is accordingly adjusted to the reference concentration.

Explanation of Operator Expression for Calculating Non-Volatile Ingredient Concentration Where the damping factor coefficient α has been determined beforehand for each of given kinds of electrodeposition paint P by establishing the relationship between ultrasonic damping factor and non-volatile ingredient concentration, the concentration measurement can be accurately calculated directly from the real-time measured damping factor according to the linearly proportional relationship, $dB = \alpha \cdot NV$, between the ultrasonic damping factor (measured in decibels dB) and the non-volatile ingredient concentration (NV), provided pH, temperature and solvent concentration are stable in the electrodeposition paint P under evaluation. Under actual conditions during a measuring procedure, however, pH and so on tend to be different from corresponding reference values obtained at the time the damping factor coefficient α is derived.

Therefore, when evaluating concentration of non-volatile ingredients in an electrodeposition paint P from a measured ultrasonic damping factor, it becomes necessary to take variations between reference-time and actual-time measured values of pH, temperature and solvent concentration into consideration. As a result of this consideration, the inventors of the present invention have discovered the following operator expression which yields an accurate calculation of non-volatile ingredient concentration, despite the aforedescribed variations:

$$NV(\%) = \{dB + \beta(\Delta t) + \gamma(\Delta pH) + \delta(\Delta c)\}/\alpha \quad (1)$$

wherein
α, in dB/NV units, is the aforementioned damping factor, which is given by dividing the ultrasonic damping factor (in dB) by the concentration of non-volatile ingredients (NV) of an electrodeposition paint P, measured according to JIS K5407;
β, in dB/Δt units, is a temperature-correction coefficient;
γ, in dB/ΔpH units, is a pH-correction coefficient;
δ, in dB/Δc units, is a solvent-correction coefficient;
Δt, ΔpH, and ΔC are the difference between reference temperature, pH, and solvent concentration, respectively, for the liquid-type material, and measured real-time values thereof; and
dB is the damping factor value of an electrodeposition paint P measured in decibels by the ultrasonic-damping factor measuring device 11.

In the foregoing, β, γ and δ are values particular to each electrodeposition paint P, as is the damping factor coefficient α.

Thus according to the operator expression, it is possible to accurately calculate non-volatile ingredient concentration, provided that α, β, γ and δ for each electrodeposition paint P to be employed are previously evaluated, and that measurements of Δt, ΔpH and Δc are made together with the ultrasonic damping factor measurement.

For each electrodeposition paint P, α, β, γ and δ can be measured according to the following method. The method is explained by reference to an example.

To begin with, five types of electrodeposition paint as indicated in Table 1 were prepared. Each electrodeposition paint is a product of Nippon Paint Co., Ltd. Then, α, β, γ and δ were evaluated for each paint.

TABLE 1

| Paint | PTU600E2 | PTU501 | PTU80 | PTU1000 | PTU2550 |
|---|---|---|---|---|---|
| Resin[1] (wt %) | 15~16 | 16~17 | 13~14 | 13~14 | 15~16 |
| Pigment[2] (wt %) | A | A | A + B[3] | A + B[4] | A |
| | 4~5 | 3~4 | 5~6 | 6~7 | 6~7 |
| Water (wt %) | 79~76 | 78~75 | 78~75 | 79~76 | 77~74 |
| Solvent (wt %) | | | | | |
| Ethyl cellosolve | — | 0.060 | 1.46 | 0.737 | 0.134 |
| Butyl cellosolve | 0.932 | 1.43 | 1.32 | 0.635 | 1.70 |
| 2-Ethyl hexanol | 0.216 | 0.198 | 0.944 | 0.157 | 0.122 |
| Hexyl cellosolve | 1.15 | 1.52 | 0.580 | 0.048 | 0.923 |
| 2-Ethylhexyl cellosolve | 0.037 | 0.013 | 0.185 | 0.571 | 0.0592 |
| Propylene glycol monophenyl ether | — | 1.18 | 0.493 | 0.108 | 0.177 |
| Total | 2.69 | 4.42 | 5.02 | 2.33 | 3.20 |

[1] Epoxy type cationic resin
[2] A and B represent carbonblack and titanium oxide, respectively
[3],[4] A:B = 1:5

Determining Damping Factor Coefficient α

A damping factor of each paint was evaluated using ultrasonic waves of 3 MHz and 2 MHz. Then, a damping factor coefficient α of each paint was calculated by dividing the damping factor by non-volatile ingredient concentration (NV) measured according to JIS K5407. The results are recorded in Tables 2 and 3.

TABLE 2

| | 3 MHz | | | | |
|---|---|---|---|---|---|
| Paint | PTU600E2 | PTU501 | PTU80 | PTU1000 | PTU2550 |
| ① Damping factor (dB) | 21.0 | 22.6 | 26.3 | 26.2 | 24.38 |
| ② JIS method NV (%) | 20.2 | 20.04 | 18.76 | 20.13 | 19.30 |
| Damping factor coefficient α ①/② (dB/NV) | 1.04 | 1.13 | 1.40 | 1.30 | 1.26 |

TABLE 3

| | 2 MHz | | | | |
|---|---|---|---|---|---|
| Paint | PTU600E2 | PTU501 | PTU80 | PTU1000 | PTU2550 |
| ① Damping factor (dB) | 15.15 | 15.53 | 17.35 | 16.10 | 16.79 |
| ② JIS method NV (%) | 20.2 | 20.04 | 18.76 | 20.13 | 19.30 |
| Damping factor coefficient α ①/② (dB/NV) | 0.750 | 0.775 | 1.925 | 0.800 | 0.870 |

Determining Temperature-Correction Coefficient β

With respect to each electrodeposition paint, the influence of temperature variation upon the damping factor was examined by using ultrasonic waves of 3 MHz while maintaining both pH and solvent concentration at reference values. The temperature-correction coefficient β was calculated by dividing the difference between the damping factor at 28° C. and at reference temperature (20° C.) by the temperature difference. The results are recorded in Table 4.

TABLE 4

| Paint | PTU600E2 | PTU501 | PTU80 | PTU1000 | PTU2550 |
|---|---|---|---|---|---|
| Damping factor (dB) | | | | | |
| ① 20° C. | 18.25 | 21.15 | 23.70 | 23.15 | 20.00 |
| ② 28° C. | 21.13 | 24.19 | 27.06 | 26.67 | 23.68 |
| Temperature-correction coefficient β(dB/Δt) ((②-①)/(28° C.-20° C.)) | 0.36 | 0.38 | 0.42 | 0.44 | 0.46 |

Determining pH-correction Coefficient γ

The influence of pH variation upon the damping factor with respect to each electrodeposition paint was examined employing ultrasonic waves of 3 MHz while maintaining both temperature and solvent concentration at reference values. The pH-correction coefficient γ was calculated by dividing the difference between the damping factor at a pH of 6.5 and at a reference pH (6.1) by the pH difference. The results are recorded in Table 5.

TABLE 5

| Paint | PTU600E2 | PTU501 | PTU80 | PTU1000 | PTU2550 |
|---|---|---|---|---|---|
| Damping factor (dB) | | | | | |
| ① pH 6.1 | 24.030 | 25.900 | 30.500 | 28.850 | 25.990 |
| ② pH 6.5 | 24.538 | 26.444 | 30.724 | 29.210 | 26.542 |
| pH-correction coefficient γ(dB/ΔpH) ((②-①)/(6.5-6.1)) | 1.27 | 1.36 | · 0.56 | 0.90 | 1.38 |

Determining Solvent-Concentration Correction Coefficient δ

For each electrodeposition paint, the influence variation in solvent concentration upon the damping factor was examined employing ultrasonic waves of 3 MHz while maintaining both temperature and pH at reference values. The solvent-concentration correction efficient δ was calculated by dividing the difference between the damping factor at 0.5% added-solvent amount and at reference concentration, i.e., at 0% added-solvent amount, by the difference in the added-solvent amounts. The results are recorded in Table 6.

TABLE 6

| Paint | PTU600E2 | PTU501 | PTU80 | PTU1000 | PTU2550 |
|---|---|---|---|---|---|
| Damping factor (dB) | | | | | |
| ① Added-solvent amount 0% | 23.90 | 23.78 | 29.01 | 26.22 | 22.60 |
| ② Added-solvent amount 1.5% | 24.84 | 24.60 | 29.90 | 26.98 | 23.76 |
| Solvent-concentration correction coefficient δ(dB/Δc) ((②-①)/(0.5-0)) | 1.88 | 1.64 | 1.78 | 1.52 | 2.32 |

It is evident from Table 4 that the temperature-correction coefficient β ranges from 0.36 to 0.46. This teaches that the coefficient β can be selected from the numbers within the range corresponding to given electrodeposition paints. Thus for the sake of simplification, 0.41, the average of the numbers ranging from 0.36 to 0.46, can be used as the coefficient β common to each electrodeposition paint. Moreover, during the foregoing pH-correction coefficient measuring procedure, pH of the paint varied by 0.4; however, it is possible to control the pH to remain within a±0.1 range, such that sudden change in pH is rare. Therefore, the pH-correction coefficient γ can be ignored under normal conditions in a measuring procedure. Furthermore, the solvent-concentration correction coefficient δ normally can also be ignored, since it is possible, in a normal electrodeposition paint vessel, to regulate variation in solvent concentration to be less than 0.1%. Consequently, the foregoing expression (1) can be simplified to the following expression (2):

$$NV\ (\%) = \{dB + X(\Delta t)\}/\alpha \qquad (2)$$

wherein the coefficient X is a number chosen from the range 0.36 to 0.46, or is simply the number 0.41.

Measurement of the concentration of non-volatile ingredients in an electrodeposition paint can be generally calculated according to expression (2), such that it is not necessary to use expression (1). Nevertheless, cases in which electrodeposition paint or water are supplied into the paint bath, or in which the substrate is small relative to the size of the electrodeposition paint vessel, and electrodeposition paint is accordingly supplied in lesser quantity, make it preferable to calculate the non-volatile ingredient concentration according to expression (1), taking into consideration variations in pH, solvent concentration and so on, which occur therein.

EXAMPLES

Example 1

Non-volatile ingredient concentration in the electrodeposition paint "PTU-2550", a product of Nippon Paint Co., Ltd., was measured at intervals of several days using the non-volatile ingredient concentration measuring apparatus of the foregoing embodiment. The same concentration was also measured according to the method defined by JIS, and the results thus obtained were compared with the results obtained employing the foregoing apparatus. These results are recorded in Table 7.

TABLE 7

| Measuring day | Example 1 (%) | JIS method (%) |
| --- | --- | --- |
| Day 1 | 20.8 | 20.8 |
| Day 7 | 20.8 | 20.6 |
| Day 10 | 20.6 | 20.4 |
| Day 15 | 20.4 | 20.6 |
| Day 24 | 20.3 | 20.4 |
| Day 37 | 20.2 | 20.3 |
| Day 38 | 20.2 | 20.1 |
| Day 49 | 20.3 | 20.4 |
| Day 56 | 20.5 | 20.9 |
| Day 59 | 20.6 | 20.6 |

As can be seen from Table 7, the results obtained by the apparatus of the present embodiment are almost the same as those obtained by the JIS method, and are accordingly shown to be reliable.

In this example, a 2500 l/min. pump, pipe lines 25 A in diameter, and a 250 mm diameter cyclone were employed in the apparatus. Also, a soaking-type transmitter "UAM-2", a product of Ultrasonic Engineering Co., LTD was used as the ultrasonic damping factor measuring device. Measuring frequency was set at 3 MHz. Coefficient X of expression (2) was set to 0.41.

Example 2

Non-volatile ingredient concentration in the electrodeposition paint "PTU80", a product of Nippon Paint Co., Ltd., was measured likewise employing the measuring apparatus used in Example 1. Herein, temperature of the electrodeposition paint was variously changed. The results are recorded in Table 8.

TABLE 8

| Elapsed time (min.) | Temperature (°C.) | Damping factor (dB) | Concentration of non-volatile ingredients (%) |
| --- | --- | --- | --- |
| 0 | 17.0 | 23.6 | 20.1 |
| 20 | 19.0 | 24.6 | 20.2 |
| 40 | 21.0 | 25.1 | 20.0 |
| 60 | 23.0 | 26.1 | 20.1 |

From Table 8, it is evident that the concentration of non-volatile ingredients remains nearly constant even under temperature changes. The results recorded in Table 8 indicate the reliability of expression (2).

Other Embodiments (a) In the foregoing embodiment, the ultrasonic damping factor measuring device 11 is employed for measuring non-volatile ingredient concentration; but flow-cell type concentration measuring equipment, such as an ultrasonic propagation-velocity measuring device and a calorimeter, can be used for the present invention in place of the measuring device 11. In this case, however, neither expression (1) nor (2) could feasibly be used, such that it would be necessary to establish other expressions corresponding to the given flow-cell type concentration measuring equipment.

(b) In the foregoing embodiment, the novel cyclone 10 is employed; however, a well-known cyclone can be used for the present invention in place of the cyclone 10.

Figure 7:
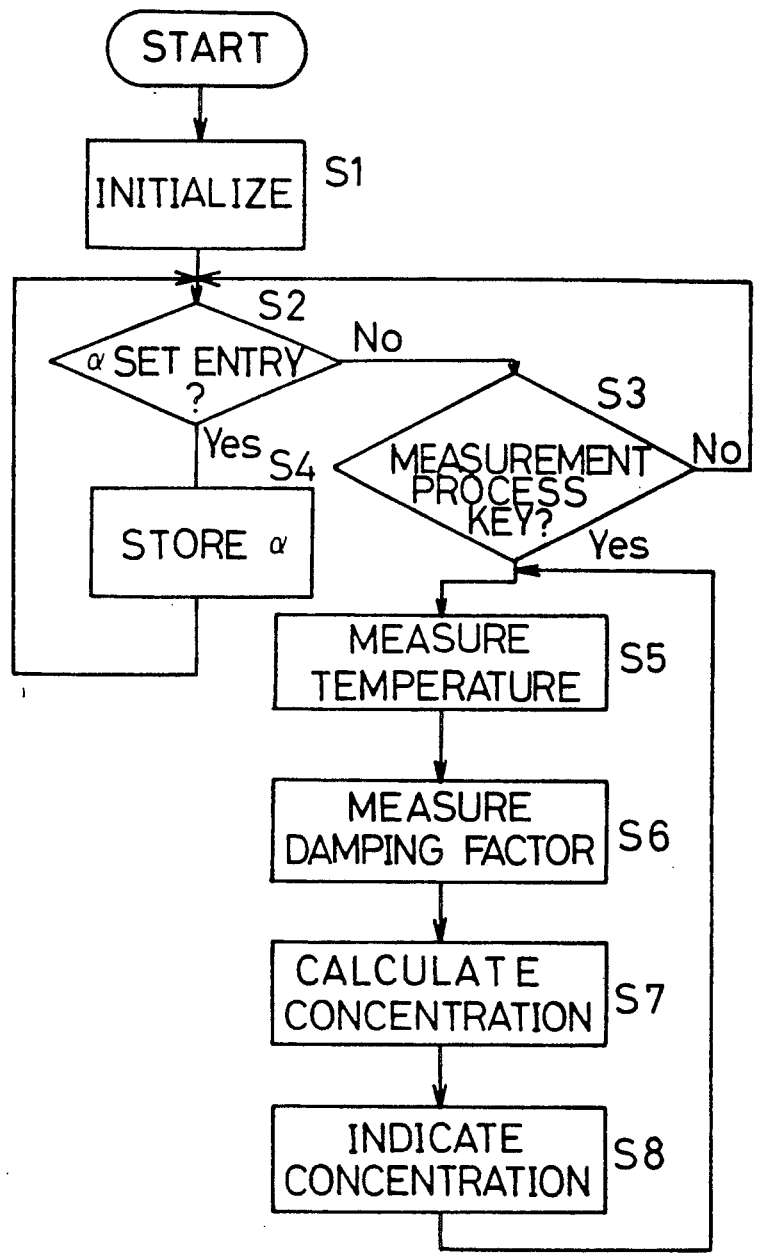
FIG. 7 is a flowchart of embodiment control processes.
Figure 8:
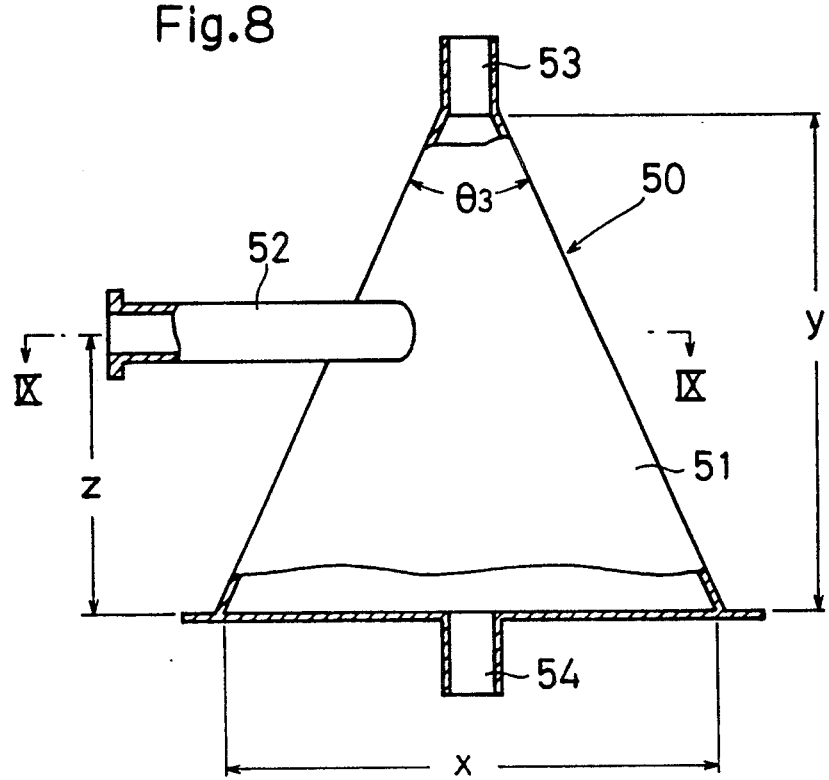
FIG. 8 is an elevational view of a cyclone according to another embodiment.
Figure 9:
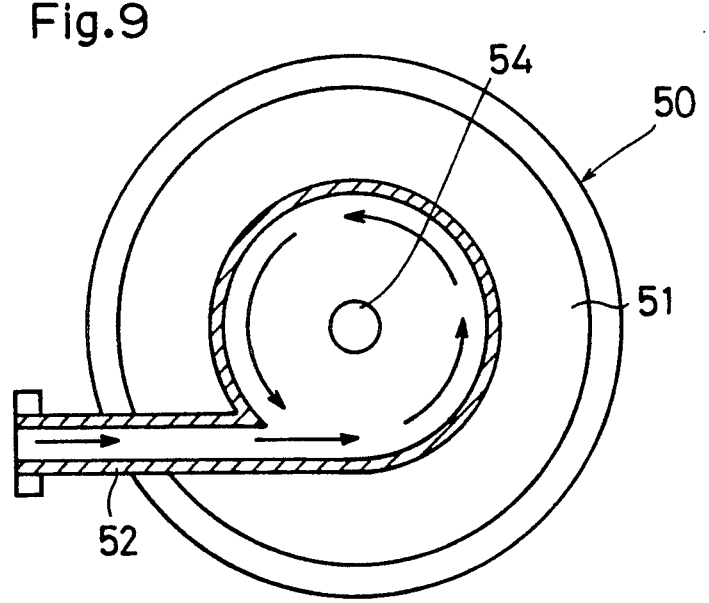
FIG. 9 is a sectional view taken along the line IX—IX of FIG. 8.

Moreover, the methods of the present invention can be performed using another novel cyclone, illustrated in FIG. 8, in lieu of the cyclone 10. Referring to FIG. 8, the cyclone 50 comprises a main body 51 formed as a hollow circular cone, and an inlet 52 which delivers electrodeposition paint P thereinto. The main body 51 has coaxial apical and central base effluent ports 53 and 54, respectively. As shown in FIG. 9, the inlet 52 projects horizontally from the main body 51, and extends tangentially along the inner circumferential surface of the main body 51, The dimensions indicated in FIG. 7 are proportioned as follows:

$$x:y = 1:1.7$$

$$z:y = 19:34$$

The apical angle $\theta_3$ of the main body 51 is made to be within the range of 30° to 90°; more preferably it is set at 60°.

Wherein the cyclone 50 is employed in the measuring apparatus 1 of the foregoing embodiment, the inlet 52, and the effluent ports 53 and 54 are connected with the feed line 13, the feedback line 15 and the manifold 14, respectively.

(c) in the foregoing embodiment, non-volatile ingredient concentration in the electrodeposition paint P is controlled by manually operating the valves 8b and 9b according to the concentration indicated on the concentration annunciator 32 in order to supply pigment and resin from the supply equipment 7 into the electrodeposition paint bath 2; however, this operation can be automated. In this case, the host computer connected to the output terminal 36 of the operational equipment 12, is further connected with the valves 8b and 9b, wherein the valves 8b and 9b can be operated according to control commands from the host computer.

(d) In the foregoing embodiment, non-volatile ingredient concentration is calculated automatically by the operational equipment 12 from the damping factor measured by the ultrasonic damping factor measuring device 11, and is indicated on the concentration annunciator 32. However, the operator of the apparatus 1 can calculate the concentration from the measured damping factor using a calculator.

(e) The measuring apparatus 1 of the foregoing embodiment is used to measure non-volatile ingredient concentration in electrodeposition paint; however, the apparatus 1 can be used for likewise measuring concentration in other liquid-type materials such as a resin suspension or a cement sludge. In these cases, either expression (1) or (2) becomes unusable, such that it would be necessary to establish other expressions according to the particular liquid-type material.

(f) Either of the novel cyclones 10 or 50 is employed in the measuring apparatus 1 of the foregoing embodiment. These cyclones 10 and 50, however, can be used for removing air bubbles contained in a pulp-preparation slurry, comprising wood chips and water, or in a slurry comprising cement and water as a raw material used in the preparation of wet-type cement.

Various details of the invention may be changed without departing from its spirit nor its scope. Furthermore, the foregoing description of the embodiment according to the present invention is provided for the purpose of illustration only, and not for the purpose of limiting the invention as defined by the appended claims and their equivalents.

We claim:

1. A method for measuring concentration of non-volatile ingredients in electrodeposition paint, comprising the steps of:

passing ultrasound through said electrodeposition paint and measuring an ultrasonic damping factor thereof; and obtaining a concentration measurement of said non-volatile ingredients from said ultrasonic damping factor by calculating according to the following expression:

$$NV(\%) = \{db + \beta(\Delta t) + \gamma(\Delta pH) + \delta(\Delta C)\}/\alpha$$

wherein

NV is present concentration of non-volatile ingredients;

$\alpha$ is a coefficient db/NV of the damping factor;

$\beta$ is a temperature-correction coefficient, $dB_\beta/\Delta\ t_\beta$, $\tau$ is a pH-correction coefficient, $dB_\gamma/\Delta\ dH_\gamma$;

$\delta$ is a solvent-concentration correction coefficient, $dB_\delta/\Delta\ C_\delta$;

$\Delta$ t is the difference between a reference temperature for said liquid material, and an actual temperature thereof, measured when said concentration measurement of non-volatile ingredients is to be obtained;

$\Delta$ pH is the difference between a reference pH for said liquid material and an actual pH thereof, measured at said time; and $\Delta$ C is the difference between a reference solvent concentration for said liquid-type material and an actual solvent concentration thereof, measured at said time.

2. A method for measuring concentration of non-volatile ingredients in electrodeposition paint, comprising the steps of:

passing ultrasound through said electrodeposition paint and measuring an ultrasonic damping factor thereof; and obtaining a concentration measurement of said non-volatile ingredients from said ultrasonic damping factor by calculating according to the following expression :ps
$$NV(\%) = \{dB + X(\Delta t)\}/\alpha$$

wherein:

NV (%) is percent concentration of non-volatile ingredients;

dB is the value of said damping factor measured in decibels;

$\Delta$t is the difference between a reference temperature of said electrodeposition paint, and an actual temperature thereof, measured when said concentration measurement of non-volatile ingredients is to be obtained; and X is a coefficient with a range of 0.36 to 0.46.

3. A method according to claim 2, further comprising the step of removing air bubbles from said electrodeposition paint.

4. A method according to claim 3, wherein said coefficient X is 0.41.

5. A method according to claim 4, wherein a cyclone is employed for said removal of air bubbles.

6. A method for controlling concentration of non-volatile ingredients contained in an electrodeposition paint, which also contains volatile ingredients and which is contained in a bath vessel, comprising the steps of:

passing ultrasound through said electrodeposition paint and measuring an ultrasonic damping factor thereof;

obtaining a concentration measurement NV of said non-volatile ingredients from said damping factor by calculating according to the expression (2) below; and supplying said volatile ingredients and said non-volatile ingredients in specific respective quantities into said bath vessel, according to the result obtained through said calculation step:

$$NV(\%) = \{dB + X(\Delta t)\}/\alpha \quad (2)$$

wherein:

NV (%) is percent concentration of non-volatile ingredients;

dB is the value of said damping factor measured in decibels;

$\alpha$ is a coefficient dB/NV of the damping factor;

$\Delta$t is the difference between a reference temperature for said liquid-type material, and an actual temperature thereof, measured when said concentration measurement of non-volatile ingredients is to be obtained; and X is a coefficient with a range of 0.36 to 0.46.

7. A method according to claim 6, further comprising the step of removing air bubbles contained in said electrodeposition paint.

8. A method according to claim 7, wherein said coefficient X is 0.41.

9. A method according to claim 8, wherein a cyclone is employed for said removal of air bubbles.

10. An apparatus for measuring concentration of non-volatile ingredients in a liquid material, comprising:

means for removing air bubbles from said liquid material, providing a bubble-purged sample thereof;

an ultrasonic-damping factor measuring means, wherein ultrasound is passed through said bubble-purged sample of said liquid material, for measuring an ultrasonic damping factor of said liquid material; and means for computing concentration of said non-volatile ingredients from said ultrasonic damping factor is provided wherein said concentration measurements of said non-volatile ingredients is made according to the expression (1):

$$NV(\%) = [dB + \beta(\Delta t) + \gamma(\Delta pH) + \delta(\Delta C)]/\alpha \quad (1)$$

wherein:

NV (%) is percent concentration of non-volatile ingredients;

dB is the decibel measurement of said ultrasonic damping factor; and $\Delta t$ is the difference between a reference temperature of said liquid material, measured when said ultrasonic damping factor is measured, and an actual temperature of said liquid material, measured at a given time of obtaining said concentration measurement of non-volatile ingredients;

$\Delta pH$ is the difference between a reference pH for said liquid material, measured when said ultrasonic damping factor is measured, and an actual pH thereof, measured at said given time;

$\Delta C$ is the difference between a reference solvent concentration for said liquid material, measured when said ultrasonic damping factor is measured, and an actual solvent concentration thereof, measured at said given time; and $\alpha$, $\beta$, $\gamma$ and $\delta$ are parameters characteristic of a specific liquid material and evaluated prior to said given time of obtaining said concentration measurement of non-volatile ingredients, said parameters being defined as follows:

$\alpha$ is a damping factor coefficient $dB_\alpha/NV_\alpha$, determined according to industry standard;

$\beta$ is a temperature-correction coefficient, $\Delta dB_\beta/\Delta t_\beta$, calculated by dividing the difference between damping factors measured at an industry-designated standard temperature and at a reference temperature by the difference between the standard temperature and the reference temperature, for constant reference pH and solvent concentration;

$\gamma$ is a pH-correction coefficient, $\Delta dB_\gamma/\Delta dH_\gamma$, calculated by dividing the difference between damping factors measure at a standard pH and at a reference pH by the difference between the standard pH and the reference pH for constant temperature and solvent concentration; and $\delta$ is a solvent-concentration correction coefficient, $dB_\delta/\Delta C_\delta$, calculated by dividing the difference between damping factors measured at a standard added-solvent concentration and at a reference added-solvent concentration by the difference between the standard added-solvent concentration and the reference added-solvent concentration.

11. An apparatus according to claim 10, wherein said liquid material is an electrodeposition paint.

12. An apparatus for measuring concentration of non-volatile ingredients in a liquid material, comprising:

means for removing air bubbles from said liquid material, providing a bubble-purged sample thereof;

an ultrasonic-damping factor measuring means, wherein ultrasound is passed through said bubble-purged sample of said liquid material for measuring in decibels an ultrasonic damping factor of said liquid material; and means for computing concentration of said non-volatile ingredients from said ultrasonic damping factor as measured by said ultrasonic-damping factor measuring means, by calculating said concentration measurement of non-volatile ingredients according to the following expression:

$$NV(\%) = [dB + X(\Delta t)]/\alpha$$

wherein

NV (%) is percent concentration of non-volatile ingredients;

dB is the decibel measurement of said damping factor;

$\Delta t$ is the difference between a reference temperature of said liquid material, measured when said ultrasonic damping factor is measured, and an actual temperature of said liquid material, measured at a given time of obtaining said concentration measurement of non-volatile ingredients; and $\alpha$, and X are parameters characteristic of a specific liquid material and evaluated prior to a given time of obtaining said concentration measurement of non-volatile ingredients, said parameters being defined as follows:

$\alpha$ is a damping factor coefficient $dB_\alpha/NV_\alpha$, determined according to industry standard, and X is a numerical coefficient ranging from 0.36 to 0.46.

13. An apparatus according to claim 12, wherein said liquid material is an electrodeposition paint.

14. An apparatus according to claim 13, wherein said calculation means comprises a sensor for measuring temperature of said electrodeposition paint.

15. An apparatus according to claim 14, wherein said calculation means further comprises means through which said coefficient $\alpha$ is received as input.

16. An apparatus according to claim 15, wherein said coefficient X is 0.41.

17. An apparatus according to claim 16, wherein said removing means is a cyclone.

18. An apparatus according to claim 17, wherein said cyclone comprises:

a cylindrical main body at vertically opposing ends of which are respective superior and inferior circular conic portions each having an apical outlet; and an inlet mounted on said superior conic portion, through which said liquid material is introduced tangentially into said main body.

19. An apparatus according to claim 17, wherein said cyclone comprises:

a main body, formed as a hollow circular cone, having respective apical and base outlets; and an inlet mounted on said main body, through which said liquid-type material is introduced tangentially thereinto.

* * * * *